(12) United States Patent
Grytdal (10) Patent No.: US 10,591,346 B2
(45) Date of Patent: Mar. 17, 2020

(54) FLUID MONITORING APPARATUS INCLUDING FLUID DENSITY DETECTION SYSTEM FOR SUBSEA APPARATUS

(71) Applicant: STATOIL PETROLEUM AS, Stavanger (NO)

(72) Inventor: Idar Olav Grytdal, Ranheim (NO)

(73) Assignee: EQUINOR ENERGY AS, Stavanger (NO)

( * ) Notice: Subject to any disclaimer, the term of this patent is extended or adjusted under 35 U.S.C. 154(b) by 144 days.

(21) Appl. No.: 15/741,640

(22) PCT Filed: Jul. 8, 2015

(86) PCT No.: PCT/EP2015/065620
§ 371 (c)(1),
(2) Date: Jan. 3, 2018

(87) PCT Pub. No.: WO2017/005322
PCT Pub. Date: Jan. 12, 2017

(65) Prior Publication Data
US 2019/0113380 A1    Apr. 18, 2019

(51) Int. Cl.
*G01F 23/28*    (2006.01)
*G01F 23/38*    (2006.01)
(Continued)

(52) U.S. Cl.
CPC .......... *G01F 23/38* (2013.01); *G01M 3/3245* (2013.01); *G01N 9/12* (2013.01); *G01N 9/18* (2013.01); *G01F 23/72* (2013.01); *G01F 23/76* (2013.01)

(58) Field of Classification Search
CPC .......... G01F 23/38; G01F 23/72; G01F 23/76; G01F 23/56; G01F 23/30; G01F 15/08;
(Continued)

(56) References Cited

U.S. PATENT DOCUMENTS 4,807,464 A * 2/1989 Janotta ................ G01M 3/3245
73/302
5,251,488 A * 10/1993 Haberman ................ G01F 1/74
73/61.44

(Continued)

OTHER PUBLICATIONS

International Search Report dated Mar. 31, 2016 in International Application No. PCT/EP2015/065620.
(Continued)

*Primary Examiner* — Harshad R Patel
*Assistant Examiner* — Nigel H Plumb
(74) *Attorney, Agent, or Firm* — Wenderoth, Lind & Ponack, L.L.P.

(57) ABSTRACT

Subsea equipment-protection apparatus including a fluid monitoring apparatus for detecting a first fluid, a second fluid and a third fluid. The fluid monitoring apparatus including a first float having a density less than that of the first fluid but greater than that of the second fluid; a second float having a density less than that of the second fluid but greater than that of the third fluid; and a sensor configured to detect the first and second floats so that the position of the floats can be determined. The first float floating when a fluid with density greater than the first float is present and sinking when a fluid with density less than the first float is present. The second float floating when a fluid with a density greater than the second float is present and sinking when a fluid with a density less than the second float is present.

15 Claims, 2 Drawing Sheets

(51) Int. Cl.
*G01M 3/32* (2006.01)
*G01N 9/18* (2006.01)
*G01N 9/12* (2006.01)
*G01F 23/72* (2006.01)
*G01F 23/76* (2006.01)

(58) Field of Classification Search
CPC ........ G01M 3/3245; G01M 3/32; G01N 9/12; G01N 9/18
See application file for complete search history.

(56) References Cited

U.S. PATENT DOCUMENTS

| | | | | |
|---|---|---|---|---|
| 2007/0186648 A1* | 8/2007 | Harmon | .................. | G01F 23/68 |
| | | | | 73/319 |
| 2014/0366627 A1* | 12/2014 | Kenney | .................. | G01F 23/68 |
| | | | | 73/308 |

OTHER PUBLICATIONS

Written Opinion of the International Searching Authority dated Mar. 31, 2016 in International Application No. PCT/EP2015/065620.

\* cited by examiner

FLUID MONITORING APPARATUS INCLUDING FLUID DENSITY DETECTION SYSTEM FOR SUBSEA APPARATUS

BACKGROUND OF THE INVENTION

1. Technical Field

The invention relates to a fluid monitoring apparatus.

It is important in many types of industry, for example in the oil and gas industry, to be able to monitor what fluids are present in a system. For example, in the oil and gas industry, in the vicinity of subsea equipment sea water is typically present. However, during leaks, hydrocarbons such as oil and gas may leak into the surrounding environment. It is desirable to detect such leaks.

2. Description of the Related Art

Previous methods of detecting such leaks have included using a monitoring apparatus that includes electrodes that can detect whether sea water, oil or gas is present. These have the disadvantage, however, of gathering salts around the electrodes that affect their performance and eventually prevent them from functioning. It is therefore desirable to provide a more reliable and robust apparatus.

SUMMARY OF THE INVENTION

The present invention provides a fluid monitoring apparatus for detecting which of a first fluid, a second fluid and a third fluid is present, the second fluid having a density less than the first fluid and the third fluid having a density less than the second fluid, the apparatus comprising: a first float having a density less than that of the first fluid but greater than that of the second fluid; a second float having a density less than that of the second fluid but greater than that of the third fluid; and a sensor, the first float being allowed to float when a fluid with density greater than the density of the first float is present and being allowed sink when a fluid with density less than the density of the first float is present, the second float being allowed to float when a fluid with a density greater than the density of the second float is present and being allowed to sink when a fluid with a density less than the density of the second float is present, and the sensor being configured to detect the first float and the second float so that the position of the floats can be determined.

Thus, the present invention allows for the detection of different fluids based upon the location of two floats with different densities. The use of floats and the physical principals of buoyancy gives an extremely reliable, robust and accurate apparatus. The simplicity of the present apparatus, for example in comparison to the prior electrode detectors, also leads to it being reliable and robust. The first float may move between a first position and a second position. In use, the first position of the first float may be an upper position and the second position may be a lower position. The second float may also move between a first position and a second position. These two positions are not necessarily the same as the two positions of the first float, indeed preferably they are different positions compared to the two positions of the first float. In use, the first position of the second float may be an upper position and the second position may be a lower position. The first and second positions may be extreme positions of the floats' displacements, the floats' displacement being limited by some limiting means.

By floating it may be understood that float is rising with respect to the remainder of the apparatus. By sinking it may be understood that the float is lowering with respect to the remainder of the apparatus.

The sensor may detect motion of the first and/or second float between the first and second positions, rather than the position of the floats themselves. Alternatively, or additionally, the position of the floats may be measured.

By fluid being present, it is meant that there is fluid in the vicinity of the fluid monitoring apparatus, i.e. fluid immediately surrounding the floats such that the presence of such a fluid would cause the floats to react accordingly under the physical laws of buoyancy.

The first and second position of the first float may be positions relative to the remainder of the apparatus (i.e. the apparatus other than the floats), or may be positions relative to the second float. The first and second position of the second float may be positions relative to the remainder of the apparatus (i.e. the apparatus other than the floats), or may be positions relative to the first float.

The displacement of the first float between the first float's first and second positions and the displacement of the second float between the second float's first and second positions may be different. This may allow the sensor to more easily detect which float is moving/has moved, for example by detecting the degree of movement of parts and comparing this to the possible displacement of the first and second float.

The floats may be formed of plastic, such as high density plastic, or resin. The floats may be formed of a high density plastic foam. Foam is particularly useful since the density of the floats can be very accurately tuned during manufacture, by simply increasing or decreasing the proportion of pores/air within the foam. During manufacture the material of the floats is selected and/or modified such that the density of the first float is between that of the density of the first and second fluids and the density of the second float is between that of the density of the second and third fluids.

The fluid monitoring apparatus may include a passageway through which fluid may pass from a first end to a second end, the passageway having a first opening at the first end and a second opening at the second end, the apparatus being arranged such that the first float and the second float may float and sink relative to the passageway in order to open and close the passageway dependent on the density of fluid present. One or both floats may hence include a seal for closing the passageway, or may be coupled to such a seal so that the seal moves when the float moves.

Thus, the fluid monitoring apparatus may act as both a fluid detector and also as an automatic fluid vent. This can be advantageous as fluid either above/below a certain threshold density can be vented to prevent build up of that fluid whilst fluid below/above that threshold can be contained. In certain circumstances, certain fluids can be retained as their spread can be undesirable/dangerous, whilst other certain fluids can be vented as their build up can be undesirable/dangerous. For instance in the field of oil and gas, it is desirable to contain an oil leak but to vent a gas leak.

The prior electrode detectors discussed above do not have such a passageway. In order to prevent build up of pressure a separate drill hole needed to be present to allow fluids to vent. The present invention does not require a separate drill hole to be present.

The passageway may have a diameter of between 5 mm and 15 mm, preferably between 6 mm and 10 mm.

In use, the first opening may be a lower opening of the passageway, and the second opening may an upper opening of the passageway. The passageway may generally extend vertically. The passageway may be defined by a sleeve, which may have any cross-section shape, but is preferably circular.

The fluid monitoring apparatus may be configured such that the second float seals the first opening of the passageway when in the first position, and the first float and the second float are distant from the first opening of the passageway when in the second positions thus allowing fluid to pass through the passageway.

In this case, when fluid of a density greater than the density of the first float (i.e. the first fluid) is present, the first and second floats will both float and may be in their first positions respectively with the first opening of the passageway sealed by a seal that is a part of or is connected to the second float. When fluid of a density less than the density of the first float but greater than the density of the second float (i.e. the second fluid) is present, the first float will sink and may be in its second position and the second float will still float and may be in its first position, the second float thus still sealing the first opening. When fluid of a density less than the density of the second float (i.e. the third fluid) is present, the first and second floats both sink and may be both in their second positions. The second float being away from its first position will move the seal away from the first opening of the passageway opening the passage way so that fluid can pass through the passageway.

When the first and/or second fluids are present, there is a positive buoyancy force acting on the second float that presses the second float upwards against the first opening of the passageway. This pressing force can add to the sealing effect.

When the first fluid is replaced by the second fluid, the first float sinks but the second float remains pressed against the first opening. When the second fluid is replaced by the first fluid then the first float will float upward.

When the second fluid is replaced by the third fluid, the second float sinks. This breaks the seal. When the third fluid is replaced by the second fluid, the second float floats. Once the second float reaches its first position, the seal may be formed.

When the first fluid is replaced by the third fluid, the first and second floats sink. This breaks the seal. When the third fluid is replaced by the first fluid, the first and second floats float. Once the second float reaches its first position, the seal may be formed.

This arrangement may be used within an oil and gas installation to release gas from a cavity in which it might otherwise build up. Thus, gas may be the third fluid, which is vented, whereas the second fluid, oil for example, is contained but its presence can be detected due to movement of the first float.

In alternative arrangement, the fluid monitoring apparatus may be configured such that the first float seals the second opening of the passageway when in the second position, and the first float and the second float are distant from the second opening of the passageway when in the first positions thus allowing fluid to pass through the passageway. Thus, the arrangement may effectively be the inverse of the above described arrangement in relation to the open and closed state of the passageway and the density of the fluid.

In this case, when fluid of a density less than the density of the second float (i.e. the third fluid) is present, the first and second floats are in their second positions respectively and the first float seals the second opening of the passageway. When fluid of a density greater than the density of the second float but less than the density of the first float (i.e. the second fluid) is present, the first float is in its second position and the second float is in its first position, the first float thus sealing the second opening. When fluid of a density greater than the density of the first float (i.e. the first fluid) is present, the first and second floats are in their first positions. The first float being away from its second position means that the second opening of the passageway is no longer sealed, and so fluid can pass through the passageway.

When the second and/or third fluids are present, there is a negative buoyancy force acting on the first float that presses the first float downwards against the second opening of the passageway. This pressing force can add to the sealing effect.

When the third fluid is replaced by the second fluid, the second float floats but the first float remains pressed against the second opening. When the second fluid is replaced by the third fluid, the second float sinks.

When the second fluid is replaced by the first fluid then the first float floats. This breaks the seal. When the first fluid is replaced by the second fluid, the first float sinks. Once the first float reaches its second position, the seal may be formed.

When the third fluid is replaced by the first fluid, the first and second floats float. This breaks the seal. When the first fluid is replaced by the third fluid, the first and second floats float. Once the first float reaches its second position, the seal may be formed.

The first fluid may be sea water, the second fluid may be oil, e.g. crude oil, and the third fluid may be gas, e.g. natural gas. The floats may hence be provided with respective densities that are between the density of oil and water, for the first float, and between the density of water and gas, for the second float. The present invention is particularly advantageous in the field of oil and gas production. The present invention can detect leaks of both oil and gas, and can differentiate between the two, in subsea locations. Further, it is possible for the apparatus to be installed into a subsea cap or the like. Such a cap may be located and configured such that rising fluid (e.g. oil/gas) may be trapped within the cap. This could lead to dangerously large pressures of gas building up. To avoid this, the venting function of the invention allows for the gas to vent. Thus, oil and gas leaks can be detected. The oil can be contained, whilst gas leaks can be vented.

The fluid monitoring apparatus of the present invention may be particularly reliable, robust and accurate when the fluids are sea water, oil and gas. The densities of sea water and oil and gas are all quite different. The inventors have recognised that using the principles of buoyancy instead of the prior-known electrode system provides a much more effective and reliable monitor for sea water, oil and gas in particular.

Of course, whilst these advantages are particularly apparent in the field of oil and gas, it should be understood that preventing building up of certain fluids, whilst containing other fluids, can be advantageous in other fields as well.

An advantage of one of the example embodiments of the invention is that it can allow for both the detection of the first and second fluid replacing the less dense third fluid, and also for the selective draining of the denser first fluid.

The first float and/or the second float may comprise an end portion and a rod portion. The rod portions of the first and second floats may both pass at least partially through the passageway. The/each end portion may be orientated perpendicularly to the rod portions. The/each end portion may comprise a planar portion that is orientated perpendicularly to the axis of the/each rod portion. The end portion of the first and/or second float may be shaped such that it may seal the passageway.

The end portion of the second float may be shaped such that it may seal the second opening of the passageway when in the second position. The end portion of the first float portion may be shaped such that it may seal the first opening of the passageway when in the first position. The/each end portion may be substantially planar in shape, and the plane may be normal to the rod. The/each end portion may be disk-shaped.

The end portion of the first float may have a greater cross-sectional area than the end portion of the second float. This arrangement may be used when the apparatus is arranged to open a passageway when the least dense fluid is present.

The end portion of the second float may have a greater cross-sectional area that the end portion of the first float. This arrangement may be used when the apparatus is arranged to open a passageway when the most dense fluid is present.

Whichever float is not performing the sealing function may have a smaller end portion than the float that is performing the sealing function. This can help to reduce the size of the apparatus. Only the end portion of the float that is performing the sealing may be required to be large enough to seal the passageway.

The first float may comprise a stopping member configured to prevent the first float from being fully withdrawn from the passageway. The stopping member may be located at an end of the rod distant from the end portion of the first float. The stopping member may be located outside of the passageway. The stopping member may be shaped such that it may prevent the first float from being fully withdrawn from the passageway.

Alternatively or additionally, the second float may comprise a stopping member configured to prevent the second float from being fully withdrawn from the passageway. The stopping member may be located at an end of the rod distant from the end portion of the second float. The stopping member may be located outside of the passageway. The stopping member may be shaped such that it may prevent the second float from being fully withdrawn from the passageway.

Thus, the stopping member can limit the extent to which the first and/or second floats float and/or sink relative to the passageway, thus at least partially defining the first and/or second positions. The limit of the relative displacement of the first/second float and the passageway may be around 10 cm, 5 cm or 1 cm.

The stopping member may comprise openings to allow fluid to pass therethrough. Thus, when the apparatus is configured to allow venting of fluid, the fluid may also freely vent through the stopping member.

The first and second floats may be configured to slide relative to one another. The rod portions of the first and second float may be configured to slide relative to one another telescopically.

In one example embodiment, the rod of the first float may protrude into the rod of the second float. This is preferably the case when it is the second float that seals against the first opening of the passageway. The first float may be nested within the second float.

In another example embodiment, the rod of the second float may protrude into the rod of the first float. This is preferably the case when it is the first float that seals against the second opening of the passageway. The second float may be nested within the first float.

The rods may generally be cylindrical in shape.

The floats may be arranged such that the rods and/or end portions are generally concentric.

In either case, the inner rod may protrude through the end portion of the outer rod, and then through the rod of the outer rod. There may be a clearance between the outer diameter of the inner rod and the diameter of the bore in the outer rod into which the inner rod is located/nested. Such a clearance may allow for fluid to enter and to be expelled from the bore as the inner rod exits and enters the bore respectively. This reduces drag on the relative motion of the floats. This clearance may be between 1 mm and 10 mm, depending on the fluid present. For example, when sea water is present, a clearance of 5 mm may be preferable.

The density of the first float may be only slightly less than the density of the first fluid, e.g. 15% less, 10% less, 5% less or 1% less. The density of the second float may be only slightly less than the density of the second fluid, e.g. 15% less, 10% less, 5% less or 1% less. The density of the first float may be only slightly greater than the density of the second fluid, e.g. 15% more, 10% more, 5% more or 1% more. The density of the second float may be only slightly greater than the density of the third fluid, e.g. 15% more, 10% more, 5% more or 1% more.

For example, when the first fluid is sea water (density of approximately 1000 kg/m$^3$), the second fluid is (crude) oil (density of approximately 800 kg/m$^3$), and the third fluid is (natural) gas (density of approximately 0.5-10 kg/m$^3$, depending on the temperature and pressure), the density of the first float may be 900 kg/m$^3$ and the density of the second float may be 300 kg/m$^3$.

The first and second floats may be each provided with a stop to limit the extent of their relative displacement. The stops may be housed within the telescoping system. The stops may comprise a groove and peg arrangement between the inner bore of the outer rod and the inner rod. The limit of their relative displacement may be around 10 cm, 5 cm or 1 cm. Thus, in use, due to the stops and the relative buoyancy of the floats, the sinking or floating of the first/second float may lead to the second/first float falling and rising with the first/second float accordingly.

When the second fluid is present, the first and second floats may be configured such that the positive buoyancy force of the second float may be greater than the negative buoyancy force of the first float. This means that, in use, when the first float sinks relative to the second float, the first float can be stopped (in its second position) and held/supported by the second float.

When the second fluid is present, the first and second floats may be configured such that the negative buoyancy force of the first float is greater than the positive buoyancy force of the second float. This means that, in use, when the second float floats relative to the first float, the second float can be stopped (in its first position) and held by the first float.

The fluid monitoring apparatus may further comprise a protective cap. The protective cap may cover the first opening. The protective cap may cover the second opening. There may be two protective caps, one covering each opening. In the case where one protective cap is present, it may cover the opening distant from the end portions of the floats, i.e. if the end portions are proximate the first opening, the end cap may cover the second opening and vice versa.

The protective cap may comprise openings for allowing fluid to pass therethrough.

The stopping member of the first and/or second float may be housed within the protective cap. The end portions of the first and second floats may be housed within the protective cap. The cap may be shaped such that it does not limit the movement of the float(s).

The sensor may comprise a magnet attached to the first and/or second float and a coil surrounding the magnet. When the floats are in a telescoping arrangement, the magnet may be attached to the inner float (only). The magnet may be a permanent magnet. Each float may comprise a magnet.

The coil may be comprised of a metal, for example copper.

The coil may surround the passageway.

The axis of the coil may extend in the direction of movement of the floats. Thus, in use, the axis of the coil may be arranged substantially vertically. The coil and the floats may be substantially concentrically arranged.

The apparatus may comprise a tube that defines the passageway. The tube may have any cross section shape, but is preferably annular in cross section. The coil may also surround the tube. The coil may be attached to the tube. In use, the axis of the tube may be substantially vertical.

In use, fluid may pass through the passageway between the inner wall of the tube and the floats. There may be a gap between the tube and the floats. The gap may be annular. The gap may be between the tube and the outer rod of the telescopic floats. There may be means, e.g. struts or elongated ridges, present in order to maintain the gap between the tube and the floats.

The coil may be housed within a coil housing, which may be a cast housing. The coil housing may be comprised of plastic material. The coil housing may have an annular cross section. In use, the axis of the coil housing may be substantially vertical. The coil housing may surround the tube. The coil housing may be attached to the tube. During manufacture, the coil may be placed around the tube and plastic may be cast onto the tube, encapsulating the coil and forming the coil housing.

The coil may be electrically connected to a connector. The connector may be suitable for connecting a cable to in order to monitor the sensor. The cable may be suitable for connecting to a subsea control module. Alternatively, the coil may be configured to be directly connected to a cable, which may connect to a subsea control module.

The sensor may use the interaction of the magnet and coil to determine a movement of the float. Take, for example, the case where the first float has the magnet attached to it, the first fluid is present and both the first and second floats are in their first positions (e.g. adjacent the first, lower opening of the passageway). When the first fluid is replaced by the second fluid, the first float may sink and the second float may remain in its first position. The first float may be stopped in its second position by its interaction with the second float. The displacement/motion of the first float may be detected by the sensor. For example, this may occur as the magnet moves relative to the coil thereby generating a voltage inside the coil. The voltage generated in the sensor may be detected by an external means connected to the sensor. The voltage can be interpreted as the first fluid being replaced by the second fluid. Other sensor means may of course be used.

When the second fluid is replaced by the third fluid, the second float may sink to its second position. The first float may sink with the second float, as it is the second float that is limiting the extent to which the first float may sink. Thus, the relative displacement between the first and the second float may be maintained at this stage. Since the first float may sink further as the second float sinks, the magnet also sinks. This movement of the magnet relative to the coil again generates a voltage. This second voltage can be interpreted as the second fluid being replaced by the third fluid.

When the third fluid is replaced by the second fluid and the second fluid is then replaced by the first fluid, the exact opposite results may occur.

It should be understood that this arrangement will work just as well when the first fluid is replaced directly by the third fluid, and vice versa. If this occurs, one larger displacement would be detected.

Take, as another example, the case where the second float has the magnet attached to it, the third fluid is present and both the first and second floats are in their second positions (e.g. adjacent the second, upper opening of the passageway). When the third fluid is replaced by the second fluid, the second float may rise and the first float may remain in its second position. The second float may be stopped in its first position by its interaction with the first float. The displacement/motion of the second float may be detected by the sensor. This may occur as the magnet passes relative to the coil generating a voltage inside the coil. The voltage generated in the sensor may be detected by an external means connected to the sensor. The voltage can be interpreted as the third fluid being replaced by the second fluid. Other sensor means may of course be used.

When the second fluid is replaced by the first fluid, the first float may rise to its first position. The second float may rise with the first float, as it is the first float that is limiting the extent to which the second float may rise. Thus, the relative displacement between the first and the second float may be maintained at this stage. Since the second float may rise further as the first float rises, the magnet also rises. This movement of the magnet relative to the coil again generates a voltage. This voltage can be interpreted as the second fluid being replaced by the first fluid.

When the first fluid is replaced by the second fluid and the second fluid is then replaced by the third fluid, the exact opposite results may occur.

It should be understood that the invention will work just as well when the third fluid is replaced directly by the first fluid, and vice versa. If this occurs, one larger displacement would be detected.

The apparatus may comprise a sealing element. The sealing element may be located between the second float and the first opening. The sealing element may be located between the first float and the second opening. The sealing element may be annular. The sealing element may surround the first/second opening. The sealing element may be attached to the first/second float. The sealing element may be attached to the remainder of the apparatus (i.e. not to one of the floats), e.g. the main body, preferably the end plate. The sealing element may comprise a resilient material, e.g. rubber. The sealing element may seal against the tube or the coil housing or the subsea equipment-protection apparatus (see below) or the main body (see below) or any other part of the apparatus (other than the other float).

The apparatus may comprise a main body. The main body may contain the passageway, the tube, the coil and/or the coil housing. The main body may be in the form of an end plate. The main body may be attached to the tube, the coil, the coil housing and/or the subsea equipment-protection apparatus or subsea cap (see below). The main body may be a socket that fits within a hole in the subsea equipment-protection apparatus or subsea cap. The plate may be proximate the first opening. The end plate may be proximate the second opening. There may be an end plate proximate each opening. The end plate may be planar. The end plate may be annular in shape. The end plate may be substantially concentric with the rod(s), the coil, the tube and/or the coil housing.

An embodiment of the invention may take the form of a subsea equipment-protection apparatus or subsea cap, the subsea equipment-protection apparatus or subsea cap comprising the fluid monitoring apparatus as described above.

The subsea equipment-protection apparatus or subsea cap may comprise a surface. The surface may comprise an opening in which the fluid monitoring apparatus is located. The surface may be unbroken in the vicinity of the opening. This may allow fluid to collect in the vicinity of the fluid monitoring apparatus. By "unbroken surface" it is meant that the surface of the cup is substantially free of holes.

The subsea equipment-protection apparatus or subsea cap may be convex. The fluid monitoring apparatus and the opening may be located in an upper portion of the surface. Again, this may allow fluid to collect in the vicinity of the fluid monitoring apparatus.

The subsea equipment-protection apparatus may be the subsea-protection apparatus described in UK patent application no. 1421016.5.

The subsea equipment-protection apparatus or subsea cap may have a hollow convex top portion. It should be noted that as used herein the reference to the top/upper parts and bottom/lower parts are with reference to the orientation of the device when in use, where the base will be closer to the sea-bed (or other underwater surface) and the top will be further from the sea-bed. Similarly, references to a vertical direction or horizontal direction are used in a manner that is consistent with this, with the horizontal being generally parallel with the sea-bed and the vertical extending normal from the sea-bed.

The hollow convex top portion may be generally dome-shaped.

The subsea equipment-protection apparatus may be placed over subsea equipment, such as a wellhead, to protect it and to gather possible leaking hydrocarbons. The subsea cap may be placed over subsea equipment to gather possible leaking hydrocarbons.

Leak-monitoring of subsea equipment is an important consideration. In known subsea equipment-protection or cap systems, no such leak-monitoring is provided. Instead, the leak-monitoring may be provided integrally as part of the subsea-equipment itself. Due to the presence of the subsea equipment-protection apparatus and the location of the fluid monitoring apparatus, leaking hydrocarbons may gather in an upper region of the subsea equipment-protection apparatus or cap. These leaking hydrocarbons, which are typically less dense than water, displace water from the upper region of the cap and may be held in the upper region of the subsea equipment-protection apparatus by the subsea equipment-protection apparatus. In this regard the dome-shaped subsea equipment-protection apparatus or cap is particularly advantageous.

The subsea equipment-protection apparatus or cap may comprise a hole in an upper portion of the subsea equipment-protection apparatus, for example a circular hole. The hole may be provided at the upper most position of the subsea equipment-protection apparatus. The hole may be provided at a center of symmetry of the subsea equipment-protection apparatus. The fluid monitoring apparatus may be located in this hole.

The subsea equipment-protection apparatus or cap may comprise a vent hole that is configured to allow small amounts of gas to vent. The hole may be separate from the apparatus of the present invention. Small amounts of gas may be given off from the sea bed and/or subsea equipment. This may be vented through the small hole to prevent the apparatus of the present invention from detecting the small amount of gas, which would effectively be a false positive for such small amounts of gas. The vent hole may be proximate the fluid monitoring apparatus.

BRIEF DESCRIPTION OF THE DRAWINGS

Certain preferred embodiments of the invention will now be described by way of example only with reference to the following drawings in which.

DETAILED DESCRIPTION OF THE INVENTION

Figure 1:
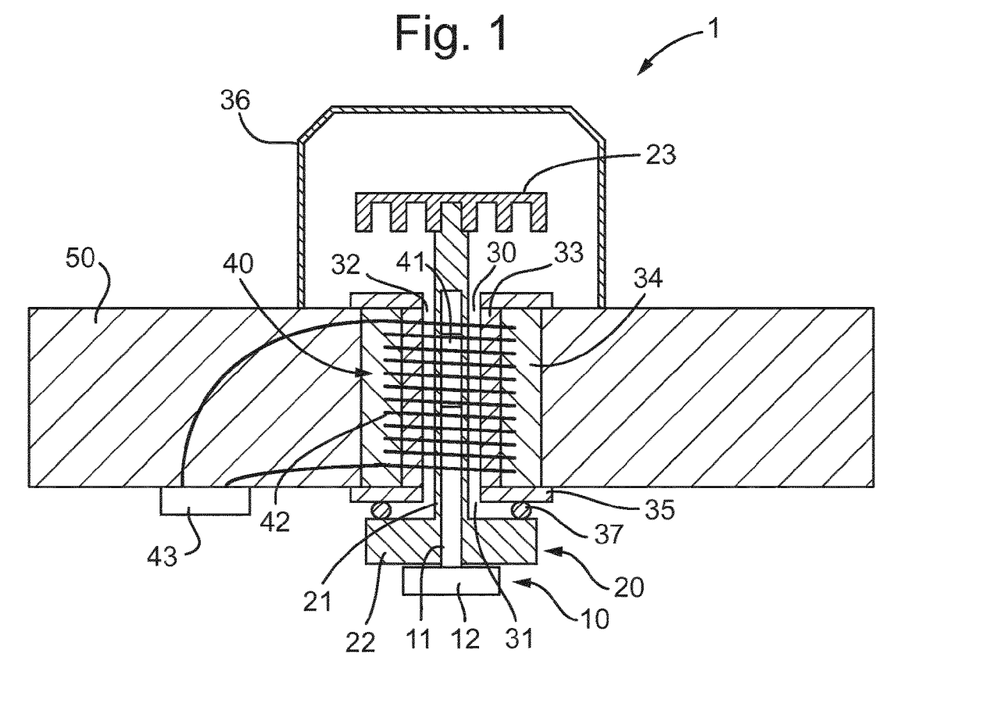
FIG. 1 shows a schematic view of an embodiment of a fluid monitoring apparatus of the present invention when a first fluid is present.

Regarding FIG. 1, a fluid monitoring apparatus 1 is shown. The fluid monitoring apparatus comprising a first float 10 and a second float 20. The first float 10 has a density less than that of sea water but greater than that of crude oil. The second float 20 has a density less than crude oil but greater than that of natural gas. In FIG. 1, sea water is present in the vicinity of fluid monitoring apparatus 1 so both the first float 10 and the second float 20 are floating in their first positions, which are their upper most positions in this embodiment.

The first float 10 comprises a rod portion 11 and a disc-shaped end portion 12. The rod portion 11 and the end portion 12 are concentric.

The diameter and thickness of the end portion 12 of the first float 10 is less than the diameter and thickness of the end portion 22 of the second float 10.

The second float 20 comprises a rod portion 21 and a disc-shaped end portion 22. The rod portion 21 and the end portion 22 are concentric. The second float 20 comprises an internal bore sized such that the rod portion 11 of the first float 10 can nest within the second float 20.

The first float 10 nests within the second float 20 and they are configured to slide relative to one another telescopically. The rods 11, 21 are substantially concentric. Between the bore of the second float 20 and the rod 11 of the first float 10 there are stops (not shown) that limits the relative displacement of the first float 10 and the second float 20.

The apparatus 1 comprises a passageway 30. The passageway has a first opening 31 at a lower end and second opening 32 at an upper end.

The rod 21 passes through the passageway from outside of the first opening 31 to outside of the second opening 32. The end portion 20 is proximate the first opening 31. The second float 20 also comprises a stopping member 23 attached to the opposite end of the rod 21. The stopping member 23 is thus proximate the second opening 32. The stopping member 23 comprises openings for allowing fluid to pass therethrough. The stopping member 23 has a diameter greater than that of the passageway 30, thus preventing the second float 20 from being fully withdrawn from the passageway 30.

The end portion 12 of the first float 10 is located proximate the first opening 31, but is located further from the first opening 31 than the end portion 22 is. The opposite end of the first float 10 is housed within the bore of the second float 20.

The passageway 30 is defined by a tube 33. The tube 33 has an annular in cross section. Surrounding the tube 33 is a coil housing 34 that also has an annular cross section. The coil housing 34 is made of plastic.

The tube 33 and the coil housing 34 are housed within a main body 35. The main body 35 comprises two end plates at opposite ends of the passageway 30. The end plates are annular disks and connect to the ends of the tube 33 and the coil housing 34. Further, when in use, as shown in FIG. 1, the end plates connect to the subsea equipment-protection apparatus 50 (only a portion of which is shown in FIG. 1).

The fluid monitoring apparatus also comprises a sensor 40. The sensor 40 comprises a permanent magnet 41 attached to the rod 11 of the first float 10, and a metal coil 42 surrounding the permanent magnet 41. The metal coil 42 is encapsulated within the coil housing 34. The rod 11, the rod 21, the passageway 30, the tube 33, the coil housing 34 and the end plates of the main body 35 are all concentric and all have their longitudinal axes orientated in a vertical direction. The metal coil 42 extends substantially over the entire length of the passageway 30. The ends of the metal coil 42 are connected via connecting wires to a connector 43 to which a cable may be connected for the signal generated in the sensor to be relayed to a controller (e.g. on the sea surface) which may alert the user to a change in fluid.

A protective cap 36 is located over the second opening 32 of the passageway 30 and over the stopping member 33 of the second float 20. The protective cap 36 has openings (not shown) for allowing fluid to pass therethrough. The protective cap allows the second float 20 to move without being impeded.

Between the upper surface of the end portion 22 of the second float 20 and the main body 35 there is a sealing ring 37. The sealing ring surrounds the first opening 31 of the passageway 30 and has a diameter greater than that of the passageway 30 but less than that of the end portion 22 of the second float 20.

Regarding FIG. 1, the apparatus 1 is shown in its configuration when sea water is present. Since both the first float 10 and the second float 20 have a density less than that of sea water, the first float 10 and the second float 20 float to their first positions. Thus, the upper surface of end portion 22 of second float 20 engages the sealing ring 37 and the passageway 30 is sealed such that no fluid can pass through the passageway 30. In this situation the rod 11 of the first float 10 is full nested within the bore of the second float 20 such that the upper surface of the end portion 12 is adjacent the lower surface of the end portion 22.

Figure 2:
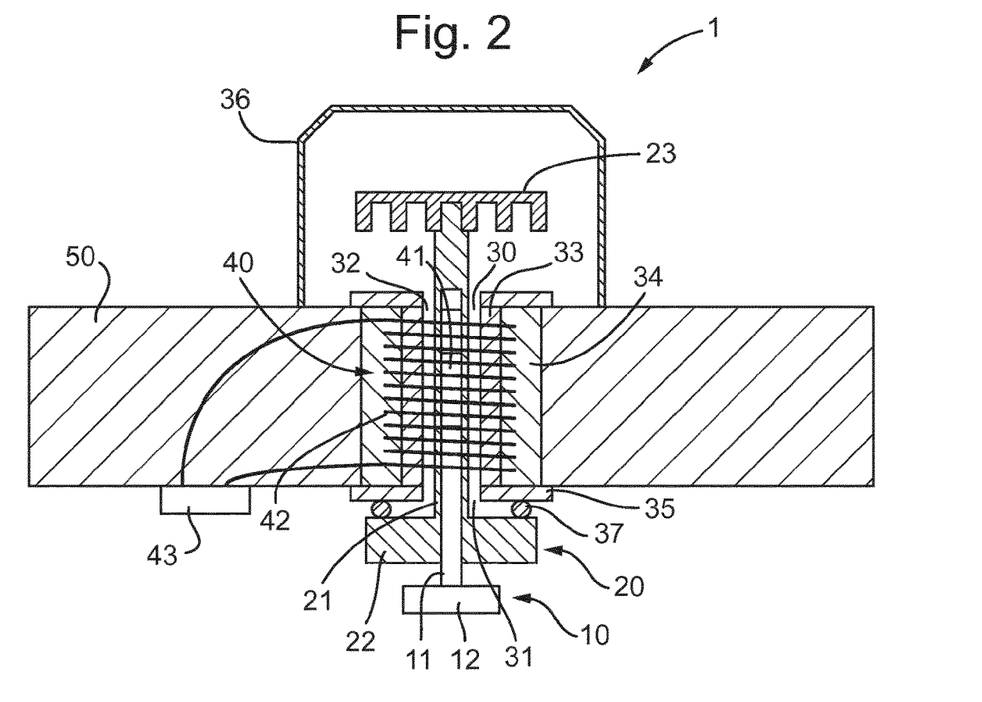
FIG. 2 shows another schematic view of the apparatus of FIG. 1 when a second fluid is present.

Regarding FIG. 2, the apparatus 1 is shown in its configuration when oil is present. Since the first float 10 is denser than oil, it has sunk to its second position. Since the second float 20 is less than oil, it remains in its first position. The first float 10 is held in its second position by the buoyancy of the second float 20 by virtue of the stops. During the sinking of the first float 10, the permanent magnet 41 has passed relative to the coil 42, thus generating a voltage. The voltage signal is relayed to the connector 43 and then preferably on to a controller. The voltage signal received at the connector 43 is indicative of only the first float 10 sinking since the voltage signal is dependent on the direction and distance of the displacement of the magnet. Thus, it is possible to detect that the first float 10 only has sunk, and hence that sea water has been replaced by oil.

Figure 3:
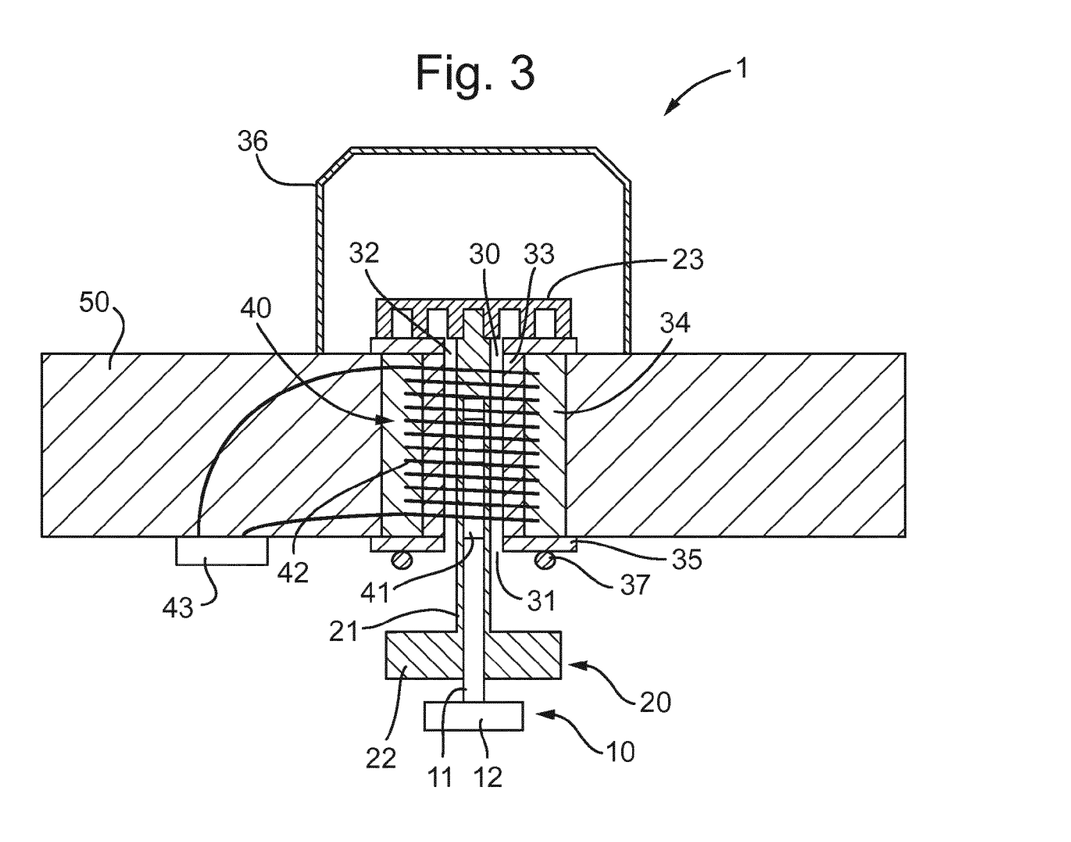
FIG. 3 shows another schematic view of the apparatus of FIG. 1 when a third fluid is present.

Regarding FIG. 3, the apparatus 1 is shown in its configuration when gas is present. Since the first float 10 and the second float 20 are less than dense than gas, they sink to their second positions. It should be noted that the first and second positions of the first float 10 are relative to the second float 20, and the first and second positions of the second float 20 are relative to the passageway. The displacement of the second float 20 is limited by the stopping member 33 and the displacement of the first float 10 is limited by the stops. During the sinking of the second float 20, the first float 10 also sinks further, thus there is further relative movement of the permanent magnet 41 and the coil 42 generating another voltage. The voltage signal is relayed to the connector 43 and then preferably on to a controller. In the case where oil is replaced by gas, the voltage signal received at the connector 43 is indicative of the second float 20 sinking since the voltage signal is dependent on the direction and distance of the displacement of the magnet. Thus, it is possible to detect that the second float 20 has sunk, and hence that oil has been replaced by gas. In the case where sea water is replaced by gas, the voltage signal is indicative of both the first float 10 and the second float 20 sinking. Thus, it is possible to detect that both the first and second floats have sunk, and hence that sea water has been replaced by gas.

Of course, as can readily be appreciated, the system works in a corresponding inverse fashion when gas is replaced by oil, or when oil is replaced by sea water, or when gas is replaced by sea water.

Further, it should readily be appreciated that the system may be inverted such that the first and second floats are arranged to seal the upper opening of the passageway. In such an embodiment, the first float and second float would sink when gas is present, the first float thus sealing the upper opening. The second float only would float when oil is present, its displacement being limited by the first float and the stops. The first float would remain sunk when the oil is present and hence continue to seal the passageway. The first and second floats would float when sea water is present, thus opening the passageway. The displacement of the first float would be limited by the stopping member. The magnet would be attached to the second float.

The invention claimed is:

1. A subsea equipment-protection apparatus comprising a fluid monitoring apparatus for detecting which of a first fluid, a second fluid and a third fluid is present, the second fluid having a density less than the first fluid and the third fluid having a density less than the second fluid, the fluid monitoring apparatus comprising:

a first float having a density less than that of the first fluid but greater than that of the second fluid;

a second float having a density less than that of the second fluid but greater than that of the third fluid; and a sensor, the first float being allowed to float when a fluid with density greater than the density of the first float is present and being allowed sink when a fluid with density less than the density of the first float is present, the second float being allowed to float when a fluid with a density greater than the density of the second float is present and being allowed to sink when a fluid with a density less than the density of the second float is present, and the sensor being configured to detect the first float and the second float so that the position of the floats can be determined.

2. The subsea equipment-protection apparatus as claimed in claim 1, comprising:

a passageway through which fluid may pass from a first end to a second end, the passageway having a first opening at the first end and a second opening at the second end, the apparatus being arranged such that the first float and the second float may float and sink relative to the passageway in order to open and close the passageway dependent on the density of fluid present.

3. The subsea equipment-protection apparatus as claimed in claim 2, the first float being allowed to float to a first position when a fluid with density greater than the density of the first float is present and being allowed sink to a second position when a fluid with density less than the density of the first float is present, and the second float being allowed to float to a first position when a fluid with a density greater than the density of the second float is present and being allowed to sink to a second position when a fluid with a density less than the density of the second float is present, the apparatus being configured such that the second float seals the first opening of the passageway when in the first position, and the first float and the second float are distant from the first opening of the passageway when in the second positions thus allowing fluid to pass through the passageway.

4. The subsea equipment-protection apparatus as claimed in claim 2, the first float being allowed to float to a first position when a fluid with density greater than the density of the first float is present and being allowed sink to a second position when a fluid with density less than the density of the first float is present, and the second float being allowed to float to a first position when a fluid with a density greater than the density of the second float is present and being allowed to sink to a second position when a fluid with a density less than the density of the second float is present, the apparatus being configured such that the first float seals the second opening of the passageway when in the second position, and the first float and the second float are distant from the second opening of the passageway when in the first positions thus allowing fluid to pass through the passageway.

5. The subsea equipment-protection apparatus as claimed in claim 2, wherein the first and/or second float comprises a stopping member configured to prevent the first and/or second float from being fully withdrawn from the passageway.

6. The subsea equipment-protection apparatus as claimed in claim 5, wherein the stopping member comprises openings for allowing fluid to pass therethrough.

7. The subsea equipment-protection apparatus as claimed in claim 1, wherein the first fluid is sea water, the second fluid is oil and the third fluid is gas.

8. The subsea equipment-protection apparatus as claimed in claim 1, wherein the first and second floats are each provided with stops configured to limit the extent of their relative displacement.

9. The subsea equipment-protection apparatus as claimed in claim 1, further comprising a protective cap.

10. The subsea equipment-protection as claimed in claim 1, comprising a surface, the surface comprising an opening in which the fluid monitoring apparatus is located.

11. The subsea equipment-protection as claimed in claim 10, wherein the surface is convex, the fluid monitoring apparatus and the opening being located in an upper portion of the surface.

12. A fluid monitoring apparatus for detecting which of a first fluid, a second fluid and a third fluid is present, the second fluid having a density less than the first fluid and the third fluid having a density less than the second fluid, the apparatus comprising:

a first float having a density less than that of the first fluid but greater than that of the second fluid;

a second float having a density less than that of the second fluid but greater than that of the third fluid;

a sensor, the first float being allowed to float when a fluid with density greater than the density of the first float is present and being allowed sink when a fluid with density less than the density of the first float is present, the second float being allowed to float when a fluid with a density greater than the density of the second float is present and being allowed to sink when a fluid with a density less than the density of the second float is present, and the sensor being configured to detect the first float and the second float so that the position of the floats can be determined;

a passageway through which fluid may pass from a first end to a second end, the passageway having a first opening at the first end and a second opening at the second end, the apparatus being arranged such that the first float and the second float may float and sink relative to the passageway in order to open and close the passageway dependent on the density of fluid present, wherein the first float and the second float each comprise an end portion and a rod portion, the rod portions of the first and second floats both passing at least partially through the passageway, the end portions of the first and second floats being orientated perpendicularly to the rod portions, and the end portion of the first and/or second float being shaped to seal the passageway.

13. The fluid monitoring apparatus as claimed in claim 12, wherein the rod portions of the first and second float may be configured to slide relative to one another telescopically.

14. A fluid monitoring apparatus for detecting which of a first fluid, a second fluid and a third fluid is present, the second fluid having a density less than the first fluid and the third fluid having a density less than the second fluid, the fluid monitoring apparatus comprising:

a first float having a density less than that of the first fluid but greater than that of the second fluid;

a second float having a density less than that of the second fluid but greater than that of the third fluid;

a passageway through which fluid may pass from a first end to a second end, the passageway having a first opening at the first end and a second opening at the second end; and a sensor, the first float being allowed to float when a fluid with density greater than the density of the first float is present and being allowed sink when a fluid with density less than the density of the first float is present, the second float being allowed to float when a fluid with a density greater than the density of the second float is present and being allowed to sink when a fluid with a density less than the density of the second float is present, the sensor being configured to detect the first float and the second float so that the position of the floats can be determined, wherein the first and/or second float comprises a stopping member configured to prevent the first and/or second float from being fully withdrawn from the passageway, wherein the first float and the second float may float and sink relative to the passageway in order to open and close the passageway dependent on the density of fluid present, and wherein the stopping member of the first and/or second float is housed within a protective cap.

15. A fluid monitoring apparatus for detecting which of a first fluid, a second fluid and a third fluid is present, the second fluid having a density less than the first fluid and the third fluid having a density less than the second fluid, the apparatus comprising:

a first float having a density less than that of the first fluid but greater than that of the second fluid;

a second float having a density less than that of the second fluid but greater than that of the third fluid; and a sensor, the first float being allowed to float when a fluid with density greater than the density of the first float is present and being allowed sink when a fluid with density less than the density of the first float is present, the second float being allowed to float when a fluid with a density greater than the density of the second float is present and being allowed to sink when a fluid with a density less than the density of the second float is present, and the sensor being configured to detect the first float and the second float so that the position of the floats can be determined, wherein the sensor comprises a magnet attached to the first and/or second float and a coil surrounding the magnet.

* * * * *